US010154820B2

(12) United States Patent
Liu et al.

(10) Patent No.: US 10,154,820 B2
(45) Date of Patent: Dec. 18, 2018

(54) METHOD AND APPARATUS FOR NAVIGATING CT SCAN WITH A MARKER

(71) Applicant: General Electric Company, Schenectady, NY (US)

(72) Inventors: Ping Liu, Beijing (CN); Jiaqin Dong, Beijing (CN); Hai Feng Wu, Beijing (CN); Meng Zhang, Beijing (CN)

(73) Assignee: General Electric Company, Schenectady, NY (US)

( * ) Notice: Subject to any disclaimer, the term of this patent is extended or adjusted under 35 U.S.C. 154(b) by 1146 days.

(21) Appl. No.: 14/090,005

(22) Filed: Nov. 26, 2013

(65) Prior Publication Data
US 2014/0148685 A1 May 29, 2014

(30) Foreign Application Priority Data

Nov. 27, 2012 (CN) .......................... 2012 1 0489836

(51) Int. Cl.
*A61B 6/03* (2006.01)
*A61B 6/00* (2006.01)
*G01R 33/54* (2006.01)

(52) U.S. Cl.
CPC .............. *A61B 6/032* (2013.01); *A61B 6/488* (2013.01); *A61B 6/542* (2013.01); *G01R 33/543* (2013.01)

(58) Field of Classification Search
CPC ......... A61B 6/032; A61B 6/488; A61B 6/542; G01R 33/543
See application file for complete search history.

(56) References Cited

U.S. PATENT DOCUMENTS

| | | | |
|---|---|---|---|
| 4,945,914 A | 8/1990 | Allen | |
| 4,991,579 A | 2/1991 | Allen | |
| 5,662,111 A | 9/1997 | Cosman | |
| 5,828,793 A * | 10/1998 | Mann | G06T 5/007 382/284 |
| 6,052,477 A | 4/2000 | Wang et al. | |
| 6,419,680 B1 | 7/2002 | Cosman et al. | |
| 6,701,007 B1 * | 3/2004 | Yamaguchi | H04N 1/6027 358/518 |
| 7,170,968 B2 * | 1/2007 | Sukovic | A61B 6/4441 378/20 |
| 7,697,738 B2 | 4/2010 | Da Silva et al. | |
| 7,902,530 B1 * | 3/2011 | Sahadevan | A61N 5/1042 250/341.7 |
| 8,027,712 B2 * | 9/2011 | Sioshansi | A61B 90/39 424/9.1 |
| 8,055,049 B2 | 11/2011 | Stayman et al. | |
| 8,830,235 B1 * | 9/2014 | Guskov | G06T 17/205 345/420 |
| 2004/0204644 A1 * | 10/2004 | Tsougarakis | G01R 33/56 600/410 |
| 2007/0003020 A1 * | 1/2007 | Hsieh | A61B 6/032 378/207 |

(Continued)

*Primary Examiner* — Baisakhi Roy
(74) *Attorney, Agent, or Firm* — McCoy Russell LLP (57) ABSTRACT

A method for a CT scan of a body part, wherein a marker is positioned on the body part. The method comprises: positioning a marker on the body part; performing a scout scan of the area which contains the body part, to acquire a scout image; detecting the marker in the scout image to acquire position information of the marker; and using the position information to navigate the CT scan.

21 Claims, 3 Drawing Sheets

(56) References Cited

U.S. PATENT DOCUMENTS

| | | | | |
|---|---|---|---|---|
| 2007/0053602 A1* | 3/2007 | Kanatsu | ............... | H04N 1/642 |
| | | | | 382/244 |
| 2007/0081704 A1* | 4/2007 | Pan | ............... | G06T 5/50 |
| | | | | 382/128 |
| 2007/0147579 A1* | 6/2007 | De Man | ............... | A61B 6/032 |
| | | | | 378/16 |
| 2007/0201610 A1* | 8/2007 | Adachi | ............... | A61B 6/032 |
| | | | | 378/4 |
| 2008/0292194 A1* | 11/2008 | Schmidt | ............... | G06T 7/0012 |
| | | | | 382/217 |
| 2009/0116719 A1* | 5/2009 | Jaffray | ............... | A61B 6/5217 |
| | | | | 382/131 |
| 2009/0268875 A1* | 10/2009 | Edlauer | ............... | A61B 6/032 |
| | | | | 378/163 |
| 2009/0299174 A1* | 12/2009 | Wright | ............... | A61B 5/06 |
| | | | | 600/424 |
| 2009/0309874 A1* | 12/2009 | Salganicoff | ............... | G06T 19/00 |
| | | | | 345/419 |
| 2013/0100165 A1* | 4/2013 | Komiyama | ............... | G09G 5/397 |
| | | | | 345/634 |
| 2014/0180065 A1* | 6/2014 | Garcia | ............... | A61B 19/54 |
| | | | | 600/424 |
| 2015/0146997 A1* | 5/2015 | Li | ............... | G06T 5/007 |
| | | | | 382/274 |

\* cited by examiner

METHOD AND APPARATUS FOR NAVIGATING CT SCAN WITH A MARKER

TECHNICAL FIELD

The present invention relates to medical scan, and particularly to a method and apparatus for navigating a CT scan with a marker.

BACKGROUND

With the development of medical technology, medical scan increasingly becomes an important tool for diagnosis and treatment in many medical applications. For example, Computed Tomography (CT) has been widely used for diagnosis examination and radiation therapy for patients. In the CT scan, as a rule, a marker will be set on the body of a patient. The marker can be used for different purposes, such as the registration between CT images and MRI images, the calibration of image alignment, or the motion correction for images, etc.

U.S. Pat. No. 8,055,049 describes a method for correcting motions of a patient during a CT scan with markers. In the method, markers are set on the patient's body in a fixed manner, then a CT scan begins, and a motion data set is obtained based on the projection positions of the markers. Lastly, a CT image is reconstructed with the motion data set.

U.S. Pat. No. 5,662,111 describes another method for using markers. In the method, markers are set at places that have relatively fixed positions with respect to tissues and structures of the patient's body, then the known coordinates of the markers are used to determine the coordinates of all the other identifiable points in the stereotactic coordinate system.

For more description of the use of markers in the medical scan, see U.S. Pat. No. 6,419,680, U.S. Pat. No. 7,697,738, U.S. Pat. No. 6,052,477, U.S. Pat. No. 4,945,914, and U.S. Pat. No. 4,991,579.

The contents of these patents are incorporated into the present application through citation.

However, in the above prior arts, markers are usually only used as reference points, and detection or application of the shape, size or orientation of the markers is not taken into consideration.

On the other hand, when performing a CT scan, scout scan needs to be performed before manually setting parameters based on the scout scan and performing the follow-up scan. However, the manual setting is inefficient, and manual factors often lead to impreciseness.

The CT scan in the prior art also involves defects in other aspects. Therefore, it is desired that there is an improved solution to increase one or more aspects of the prior art, e.g. to improve the use of the markers, or increase the efficiency and preciseness of parameter settings.

SUMMARY OF THE INVENTION

Embodiments of the present invention solve one or more problems existing in the prior art, in particular, to improve the use of markers, realize the auto-navigation of CT scan and/or increase the efficiency and preciseness of the scan parameter settings.

According to one aspect of the present invention, a method for a CT scan of a body part is provided, wherein a marker is positioned on the body part. The method comprises performing a scout scan of the area that contains the body part to acquire a scout image, detecting the marker in the scout image to acquire position information of the marker, and using the position information to navigate the CT scan.

According to one embodiment, the marker is a wire-like marker which is positioned on the body part to be parallel to Z-axis of the CT scan.

According to one embodiment, using the position information to navigate the CT scan comprises using the position information to set a Z-axis scan range in the CT scan, and/or using the position information to set a Y-axis scan range in the CT scan, and using the Z-axis scan range and/or the Y-axis scan range to perform the CT scan.

According to one embodiment, the position information is used to set a Y-axis scan range for the CT scan in a D4D-CT scan.

According to one embodiment, the Z-axis scan range in the CT scan is set based on the positions of two endpoints of the wire-like marker and start position of the scout scan.

According to one embodiment, detecting the marker in the scout image to acquire the position information of the marker comprises: applying a linear difference operator to the scout image at least once to acquire an enhanced image, wherein the linear difference operator is determined based on shape and orientation of the marker.

According to one embodiment, detecting the marker in the scout image to acquire the position information of the marker comprises pre-processing the enhanced image, and the pre-processing comprises: removing redundant information from the enhanced image; segmenting the image that has the redundant information removed.

According to one embodiment, removing the redundant information from the enhanced image comprises: identifying pixel points whose pixel values are below the preset threshold as background; and/or segmenting the image that has the redundant information removed comprises: adding average value of the image that has the redundant information removed to standard deviation thereof.

According to one embodiment, the segmented image is processed in the following steps: based on the shape and orientation of the marker, removing noise of a candidate graphic in the image, and filling gaps of the candidate graphic; and slenderizing the candidate graphic.

According to one embodiment, detecting the marker in the scout image to acquire the position information of the marker comprises: performing pattern recognition on the pre-processed image so as to acquire the position information of the marker in the image space of the scout image.

According to one embodiment, the pattern recognition is at least based on one of: physical length of the marker, shape of the candidate graphic in the image, and whether there are other graphics on an extension line of the candidate graphic.

According to one embodiment, detecting the marker in the scout image to acquire the position information of the marker further comprises: converting image position information of the marker in the image space of the scout image to physical position information of the marker in the CT scan system.

According to a second aspect of the present invention, an apparatus for a CT scan of a body part is provided, wherein a marker is positioned on the body part. The apparatus comprises: a scout scan component for performing scout scan of the area that contains the body part to acquire a scout image; a position acquisition component for detecting the marker in the scout image to acquire position information of the marker; a navigation component for using the position information to navigate the CT scan.

According to a third aspect of the present invention, a method for a medical scan of a body part is provided, wherein a marker is positioned on the body part. The method comprises: performing a scout scan of the area that contains the body part to acquire a scout image; detecting the marker in the scout image to acquire position information of the marker; and using the position information to navigate the medical scan.

The improved solution of the present invention can solve one or more problems existing in prior art. Through the present invention, information such as the shape and orientation of the marker in the scout scan can be fully utilized to realize the auto-navigation of the CT scan, and/or to increase the efficiency and preciseness of parameter settings.

BRIEF DESCRIPTION OF THE FIGURES

The advantages, characteristics and features of the present invention can be further understood through the following descriptions of modes of carrying out the present invention in combination of the Figures. The Figures comprise.

DETAILED DESCRIPTION OF THE INVENTION

Embodiments of the present invention will be described with reference to the Figures. The Figures illustrate demonstrative embodiments of the present invention. However, the present invention is achievable in other different forms, and shall not be understood to be only limited to these specifically stated embodiments. To the contrary, these embodiments are provided to make the disclosure of the present invention so thorough and complete as to fully convey the concept of the present invention to those skilled in the art. In the whole text, the same or similar number indicates the same device or unit.

Figure 1:
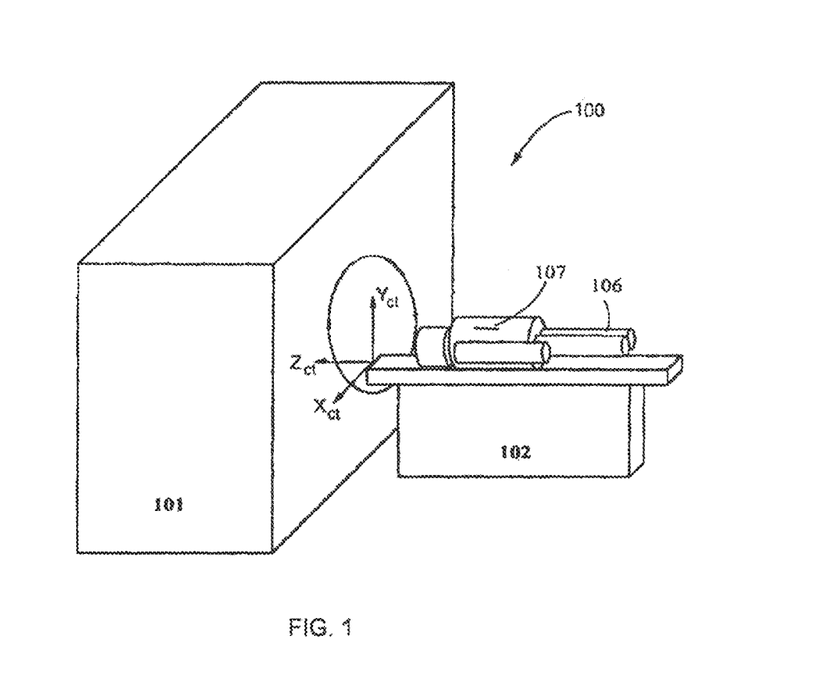
FIG. 1 illustrates a CT scan system according to one embodiment of the present invention.

FIG. 1 demonstratively shows a CT scan system 100 according to one embodiment of the present invention. The CT scan apparatus system 100 comprises a CT apparatus 101 and a CT examination table 102 for placing a patient 106. The CT apparatus 101 is used for obtaining the CT data of the patient 106. FIG. 1 also illustrates a marker 107. As illustrated in FIG. 1, in the three dimensional coordinate system used in the CT scan system 100, the X-axis is parallel to the surface of the examination table and is perpendicular to the long side of the surface of the examination table, the Y-axis is perpendicular to the surface of the examination table, and the Z-axis is parallel to the long side of the surface of the examination table. Such setting of a coordinate system is often used in the art, and there is no necessity for elaboration herein.

Figure 2:
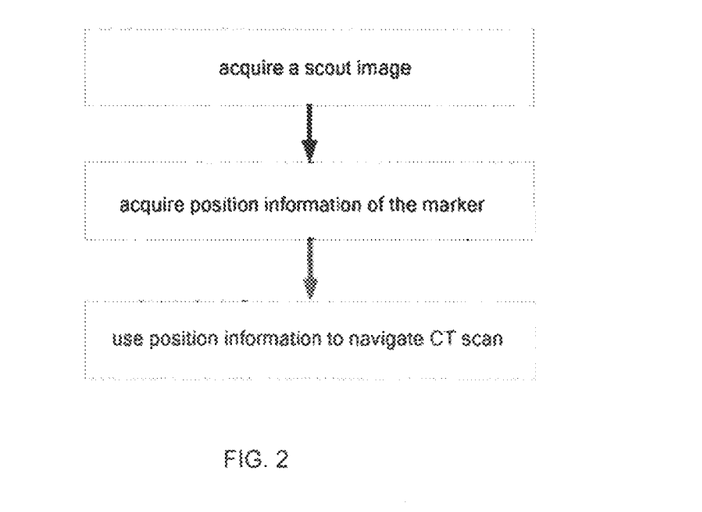
FIG. 2 illustrates a method of automatically navigating a CT scan with markers according to one embodiment of the present invention.

FIG. 2 illustrates a method of auto-navigating the CT scan with a marker according to one embodiment of the present invention, wherein a marker is positioned on the body part of the patient to be scanned. In the method, a scout scan of the area that contains the body part to be scanned needs to be performed first to acquire a scout image, then the marker in the scout image is detected to acquire the position information of the marker, finally, the acquired position information is used to navigate the CT scan.

Usually, markers are made of metals or other materials having relatively higher CT values, thus imaging of the markers can be performed through a CT scan, and obvious artifacts can be avoided as well. As illustrated in FIG. 1, a marker 107 is formed in a wire-like shape, and has length and width that can change according to specific applications. However, the markers in the present invention are not limited to wire-like markers. According to other embodiments, markers can be diamond, round, oval or in other shapes suitable to be detected in the scout image. Moreover, although the marker illustrated in FIG. 1 is parallel to the Z-axis of the CT scan system, it is understandable that other orientations of the marker are feasible as well, e.g. the marker is set to be slantwise with respect to the Z-axis.

According to one embodiment, detecting the marker in the scout image means detecting the marker as a whole, e.g. when the overall shape and orientation of the marker are taken into consideration, detecting the positions of all points of interest on the marker, rather than simply detecting the positions of individual points on the marker.

Figure 3:
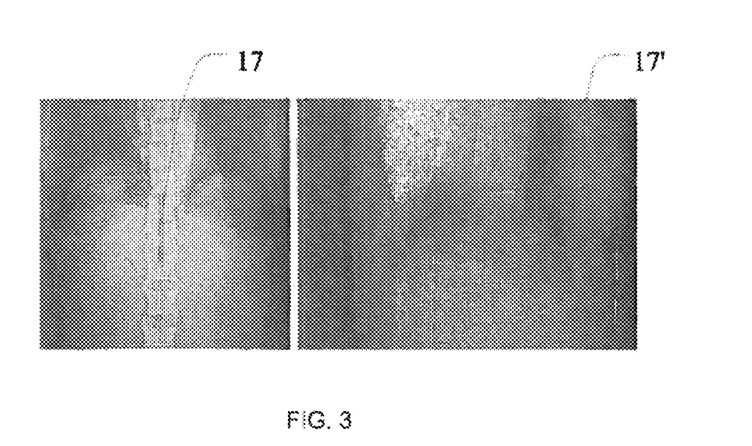
FIG. 3 illustrates a 0 degree scout image and a 90 degree scout image according to one embodiment of the present invention.

In the process of the scout scan, a low dose of X-ray is used to scan the body area that contains the target part to be scanned to acquire the scout image. A 0 degree scout image and a 90 degree scout image can be obtained through the scout scan. The left view of FIG. 3 illustrates the 0 degree scout image, which shows the view parallel to the X-Z plane, wherein the relevant position information 17 of the marker on the X-axis and the Z-axis is reflected. The right view of FIG. 3 illustrates the 90 degree scout image, which shows the view parallel to the Y-Z plane, wherein the relevant position information 17' of the same marker on the Y-axis and the Z-axis is reflected. Since the scout scan and the acquisition of the scout image are widely known in the art, there is no necessity for elaboration herein. It is understandable that in the present invention, a 0 degree scout image and a 90 degree scout image can be acquired concurrently according to practical applications, or only either of the images is acquired.

According to one embodiment of the present invention, using the position information of the marker to navigate the CT scan comprises using the position information to set the Z-axis scan range and the Y-axis scan range in the CT scan. The marker is fixed on the body part to be scanned, and there is a corresponding position relation between the marker and the body part to be scanned, e.g. the two endpoints of the wire-like marker can be respectively corresponding to the start position and end position of the body part (or area) to be scanned on the Z-axis. Alternatively, the 90 degree scout image can reflect the Y-axis position information of the body part to be scanned at each position on the Z-axis. Through an overall detection of the marker, the position signals of all points of interest on the marker (or the points needed for navigating the CT scan) can be obtained. Therefore, the overall position information of the marker can be utilized to set the scan range of the Z-axis and/or Y-axis.

According to one embodiment of the present invention, in D4D-CT scan, the position information of the marker is used to set the Y-axis scan range in the CT scan, such that the breathing cycle measurement can be performed accurately. It is understood that the setting of the Y-axis scan range can also be applied to scan of other types according to practical situations. Using the Y-axis position information of the part to be scanned to set the Y-axis scan range of D4D-CT scan is quite often in the art, and there is no necessity for elaboration herein, either.

According to one embodiment of the present invention, the two endpoints of the wire-like marker respectively correspond to the start position and end position of the body part to be scanned. For example, as illustrated in FIG. 1, the part to be scanned is between the two parallel planes that pass the two endpoints of the wire-like marker and are perpendicular to the Z-axis. Therefore, adding the Z-axis coordinate of the two endpoints of the wire-like marker to the Z-axis coordinate of the physical position where the scout scan starts can reach the Z-axis scan range of the next CT scan.

According to one embodiment of the present invention, when the marker is not a wire-like marker (e.g. a diamond marker), specific positions (e.g. the two acute vertexes of the diamond) of the not wire-like marker can be made to correspond to the start position and end position of the body part to be scanned so as to set the Z-axis scan range of next CT scan in a similar manner to that mentioned above.

Using the position information of the marker to navigate the CT scan comprises not only setting the CT scan range of the Z-axis and Y-axis, but also setting some other scanning parameters relevant to the marker.

In the present invention, there are various ways to detect the marker in the scout image to acquire the position information. Although these detecting ways are different in specific implementations, it is understandable that as long as graphics or objects in the image can be detected and their position can be determined in these ways, these ways should be included in the scope of the present invention.

According to one embodiment of the present invention, detecting a marker in the scout image to acquire the position information of the marker comprises: applying a different operator to the scout image to acquire an enhanced image, which can be realized by using the difference operator to calculate derivatives for the scout image. The difference operator can be selected based on the shape and orientation of the marker. For a wire-like marker, when determining the difference operator, the shape information can be used by estimating the wire width of the imaging of the marker in the scout image. For example, if a 1.5 mm wide wire-like marker is used in D4D-CT scan, then the width of its projection can be about 2 pixels. Such setting brings good performance to the marker detection. In addition, the orientation of the marker can be considered as well. Usually, the orientation of wire-like markers on human body is parallel to the Z-axis.

Figure 4A:
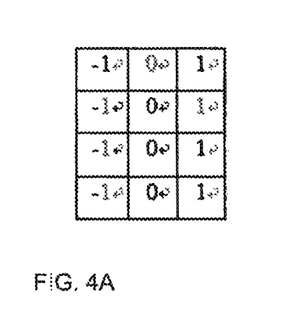
FIG. 4A illustrates a difference operator based on the shape and orientation of the marker according to one embodiment of the present invention.
Figure 4B:
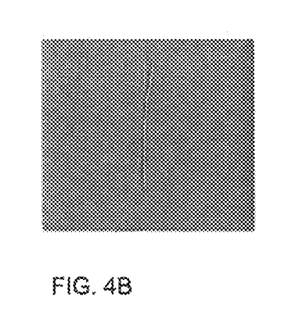
FIG. 4B illustrates an image obtained after applying a difference operator to the scout image according to one embodiment of the present invention.

FIG. 4A illustrates a difference operator determined based on the shape and orientation of the marker according to one embodiment of the present invention. The wire-like difference operator can be corresponding to the wire-like marker which is set to be parallel to or approximately parallel to the Z-axis and have a width of 1.5 mm. FIG. 4B illustrates the enhanced image obtained by applying the difference operator to the scout image. As can be seen, the candidate graphic of the wire-like marker in the scout image is enhanced, but the other parts are depressed.

FIGS. 4A and 4B illustrate a specific difference operator, but the present invention is not limited thereto. In accordance with the practical shape and orientation of the marker, operators having different numerical values or patterns can be used to calculate the first derivative, the second derivative or even higher derivatives (if needed) of the scout image to obtain the enhanced image. Using difference operators to calculate derivatives of images is widely known in the art, and there is no necessity for elaboration herein.

According to one embodiment of the present invention, after applying a difference operator to the scout image to acquire an enhanced image, further pre-processing can be performed on the enhanced image. Pre-processing comprises but is not limited to: removing the redundant information from the enhanced image and segmenting the image that has the redundant information removed.

According to one embodiment, removing the redundant information means removing redundant and subtle information from the smooth area (i.e. area without edges or candidate graphics) of the image, which can be realized by identifying pixel points whose pixel values are below the preset threshold as background. By setting a safe preset threshold, most of the redundant and subtle information can be removed, thus the data amount in subsequent steps can be dramatically reduced. When selecting the preset threshold, different or same preset threshold can be used for the 0 degree scout image or the 90 degree scout image. In addition, a relatively low (e.g. 50) threshold can be selected to ensure that the remained information can contain the needed candidate graphic or edge completely.

According to one embodiment, an automatic threshold can be further used to segment the image that has the redundant information removed, namely, the average value of the image that has the redundant information removed is added to the standard derivation thereof. The specific formula goes as follows:

$$T = \text{AVE(image)} + \text{STD(image)} \tag{1}$$

wherein AVE (image) indicates the average value of the image that has the redundant information removed, STD (image) indicates the standard derivation of the image that has the redundant information removed, and T indicates the segmented image. After the image is segmented, e.g. for wire-like markers, the data information that mainly represents edges in a wire-like or similar shape can be obtained.

According to one embodiment of the present invention, pre-processing can also comprise further processing the segmented image, wherein based on the shape and orientation of the marker, an image morphology algorithm is used to remove the noise of the candidate graphic of the imaging of the marker in the image, the gaps of the candidate graphic are filled, and/or the candidate graphic of the marker is slenderized.

In one embodiment, a graphics approximation algorithm is used to remove the noise and fill the gaps of the candidate graphic. When designing the approximation operator of the graphics approximation algorithm, the shape and orientation of the marker can be considered as well. For example, for a wire-like marker, its wire width and direction can be considered. The graphics approximation algorithm is often used in image morphologies, and there is no necessity for elaboration herein.

In one embodiment, a horizontal slenderization algorithm is used to slenderize the candidate graphic of the wire-like marker in the image. For a wire-like marker, slenderization can make all graphics in the image become vertical or approximately vertical. Horizontal slenderization algorithm is often used in graphic morphologies as well, and there is no necessity for elaboration herein.

Figure 5:
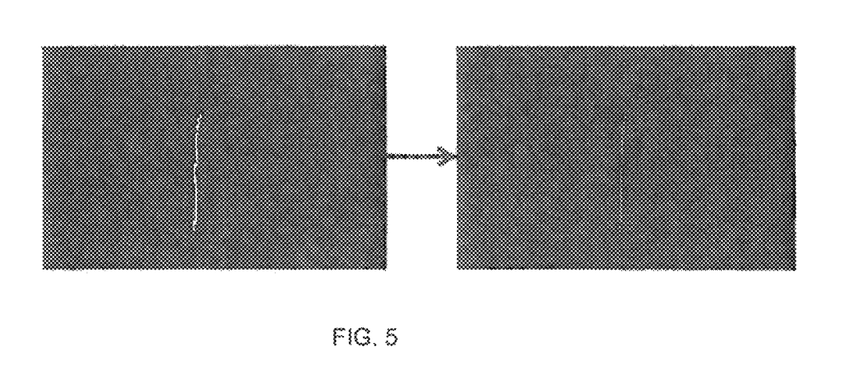
FIG. 5 illustrates the candidate graphic before and after slenderizing according to one embodiment of the present invention.

FIG. 5 illustrates the changes of the candidate graphic of the marker before and after slenderization, wherein the left view of FIG. 5 shows the situation after image segmentation and graphics approximation algorithm are performed, whereas the right view shows the situation after further slenderization processing is accomplished.

Figure 6:
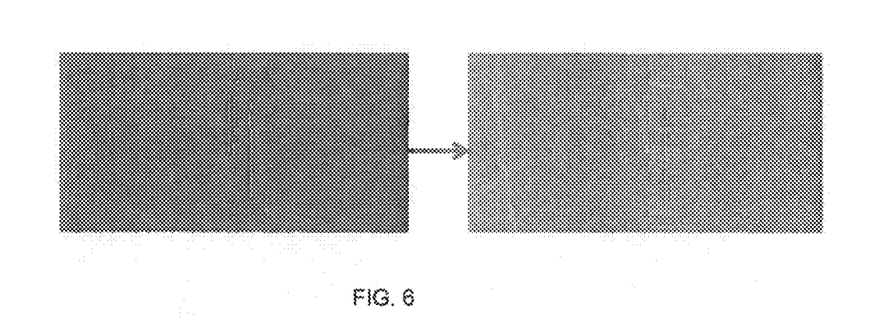
FIG. 6 illustrates the result of pattern recognition algorithm in the presence of noise according to one embodiment of the present invention.

According to one embodiment of the present invention, the pattern recognition is performed on the pre-processed image to acquire the image position information of the marker in the image space of the scout image. Firstly, all candidate graphics in the pre-processed image is counted, and then a marker pattern recognition algorithm is used to select the candidate image which has the highest pattern score, e.g. the pattern recognition can be at least based on one of: physical length of the marker, shape of the candidate graphic in the image, and whether there are other graphics on an extension line of the candidate graphic, etc. It is understandable that other parameters can be used in the pattern recognition as well. FIG. 6 illustrates that in the presence of noise, correct result can be ensured through the pattern recognition algorithm as well.

According to one embodiment, for a wire-like marker, the formula for calculating the pattern score value goes as follow:

$$Sn = a*\text{LEN}(Ln) + b*\text{EXT}(Ln) + c*\text{LIN}(Ln)+ \quad (2)$$

wherein, Sn indicates the pattern score value of the nth candidate linear graphic; LEN (Ln) indicates the similarity to the wire length, wherein the more the length of the candidate linear graphic approximates the real wire pattern, the higher the score value; EXT (Ln) indicates that on the extension lines on both sides of the candidate graphic, there should be no more line segments; LIN (Ln) indicates the linearity of the real wire-like marker. Since the wire-like marker is fixed to the soft and flexible body of the patient, the candidate graphic in the 90 degree scout image should not be a standard straight line; in addition, a, b, c indicate the weight coefficients of various factors. The corresponding pattern score value of each candidate graphic can be obtained through said formula (2).

It is understandable that formula (2) is only demonstrative. For a specific marker, other factors of the marker can be used to calculate the pattern score value as well, or some of the factors therein is not taken into consideration by setting the weight coefficients to be zero.

After obtaining the corresponding pattern score value of each candidate graphic, as a rule, the candidate graphic which has the biggest pattern score value is identified as the imaging of the marker, and the image position information of the imaging of the marker in the scout image is determined. However, according to one embodiment of the present invention, optionally, the identified result can be judged according to the real shape of the marker. For example, for a wire-like marker, if the identified wire length does not satisfy the maximum or minimum requirement for wire length, then the identified result is ignored, and it is reported to the system that no marker is detected.

According to one embodiment of the present invention, the image position information of the marker in the image space can be converted to the physical position information of the marker in the CT scan system. By means of the relationship between the image space and the actual physical space (e.g. 2 pixels represents the physical distance of 1.5 mm), the conversion between the image position and the physical position can be realized in various ways. For example, the image space as a whole is converted to the physical space, and then the position information of the marker in the CT scan system is determined. Alternatively, only the whole position of the identified marker in the image space is converted to the actual physical position. Even, only the image positions of points of interest on the imaging of the marker are converted to the physical positions, e.g. only the image positions of the two endpoints of the identified wire-like marker are converted to the physical positions.

Compared with other methods for detecting markers in the scout image to acquire the position information, the above introduced detection method of the present invention is more robust and more accurate.

After obtaining the physical position information of the marker, the position information can be used to navigate the CT scan. For example, the Z-axis scan range of subsequent CT scan can be set according to the physical positions of the two endpoints of the wire-like marker. Moreover, the Y-axis coordinate corresponding to each position on the Z-axis of the marker can be obtained in the 90 degree scout image. The information can be used to precisely navigate the D4D-CT scan.

Figure 7:
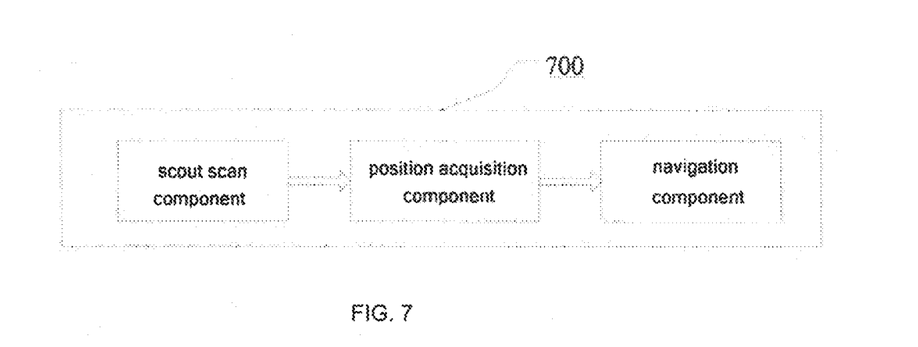
FIG. 7 illustrates an apparatus for CT scan according to one embodiment of the present invention.

FIG. 7 illustrates an apparatus 700 for the CT scan according to one embodiment of the present invention, wherein a marker is positioned on the body part. The apparatus comprises: a scout scan component for performing scout scan of the area that contains the body part to acquire a scout image; a position acquisition component for detecting the marker in the scout image to acquire the position information of the marker; a navigation component for using the position information to navigate the CT scan.

In an apparatus according to one embodiment, the navigation component is configured to use the position information to set the Z-axis scan range in the CT scan, and/or use the position information to set the Y-axis scan range in the CT scan, wherein the Z-axis scan range and/or the Y-axis scan range is used for the CT scan.

In an apparatus according to one embodiment, the position information is used to set the Y-axis scan range in the CT scan in D4D-CT scan.

In an apparatus according to one embodiment, the Z-axis scan range in the CT scan is set based on the positions of the two endpoints of the wire-like marker and the start position of the scout scan.

In an apparatus according to one embodiment, the position acquisition component is configured to apply at least one linear difference operator to the scout image to acquire the enhanced image, wherein the at least one linear difference operator is acquired on the basis of the shape and orientation of the marker.

In an apparatus according to one embodiment, the position acquisition component is configured to pre-process the enhanced image, and the pre-processing comprises: removing redundant information from the enhanced image; and segmenting the image that has redundant information removed.

In an apparatus according to one embodiment, removing redundant information from the enhanced image comprises: identifying pixel points whose pixel values are below a preset threshold as background; and/or segmenting the image that has redundant information removed comprises: adding the average value of the image that has redundant information removed to the standard derivation thereof.

In an apparatus according to one embodiment, the segmented image is processed in the following steps: based on the shape and orientation of the marker, using an image morphology algorithm to remove the noise of the candidate graphic of the imaging of the marker in the image, and filling the gaps of the candidate graphic; and/or slenderizing the candidate graphic.

In an apparatus according to one embodiment, the position acquisition component is configured to perform a pattern recognition on the pre-processed image so as to acquire the position information of the marker in the image space of the scout image.

In an apparatus according to one embodiment, the pattern recognition is at least based any one of: length of the marker, shape of the candidate graphic, and whether there are other objects on the extension line of the candidate graphic.

In an apparatus according to one embodiment, the position acquisition component is further configured to convert the image position information of the marker in the image space of the scout image to the physical position information of the marker in the CT scan system.

It is also understandable to those skilled in the art that the present invention is also applicable to other types of medical scans besides the CT scan, including but not limited to Magnetic Resonance Imaging scan, etc. The scout image in CT is called "scout", whereas the scout image in MRI is called "plain film". Accordingly, the present application also discloses a method for medical scan, including: performing a scout scan of the area that contains the body part to acquire a scout image; detecting the marker in the scout image to acquire the position information of the marker; and using the position information to navigate the medical scan.

In a medical scan method according to one embodiment, using the position information to navigate the medical scan comprises: using the position information to set the Z-axis scan range of the medical scan, and/or using the position information to set the Y-axis scan range of the medical scan; and using the Z-axis scan range and/or the Y-axis scan range for the medical scan.

In a medical scan method according to one embodiment, the Z-axis scan range of the medical scan is set based on the positions of the two endpoints of the wire-like marker and the start position of the scout scan.

It is understandable to those skilled in the art that the present invention can be carried out in various ways known in the art, including but not limited to: hardware, firmware, computer program, and logic devices, etc.

By means of the above explanations and the corresponding figures, optimal embodiments of the present invention have been disclosed in details. In addition, although some specific terms are used in the description, they are just demonstrative. Those skilled in the art will comprehend, and can apply various modifications, equivalent replacement and variations to the present invention. For example, one step or module in the embodiments is divided into two or more steps or modules, or to the contrary, the functions of two or more steps, modules or apparatuses in the embodiments are incorporated into one step or module. As long as the transformations are not away from the spirit of the present invention, they shall fall into the protection scope claimed by the present application. The protection scope of the present invention depends on the attached claims.

This written description uses examples to disclose the invention, including the best mode, and also to enable any person skilled in the art to practice the invention, including making and using any computing system or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for a CT scan of a body part, wherein a marker is adapted to be positioned on the body part, the method comprising:
    performing a scout scan of an area that contains the body part with the marker positioned thereon to acquire a scout image;
    automatically detecting the marker in the scout image to acquire position information of the marker; and
    performing the CT scan of the body part while using the position information of the marker to navigate the CT scan.

2. The method according to claim 1, wherein the marker is a wire-like marker which is positioned on the body part to be parallel to a Z-axis in a CT scan system.

3. The method according to claim 2, wherein using the position information of the marker to navigate the CT scan comprises:
    using the position information of the marker to set a Z-axis scan range in the CT scan, and/or using the position information of the marker to set a Y-axis scan range in the CT scan; and
    using at least one of the Z-axis scan range and the Y-axis scan range to perform the CT scan.

4. The method according to claim 1, wherein detecting the marker in the scout image to acquire the position information of the marker comprises applying a linear difference operator to the scout image at least once to acquire an enhanced image, wherein the linear difference operator is determined based on a shape and an orientation of the marker.

5. The method according to claim 4, wherein detecting the marker in the scout image to acquire the position information of the marker comprises pre-processing the enhanced image, wherein the pre-processing comprises:
    removing redundant information from the enhanced image; and
    segmenting the image that has had the redundant information removed.

6. The method according to claim 5, wherein removing the redundant information from the enhanced image comprises at least one of:
    identifying pixel points with pixel values that are below a preset threshold as background; and
    segmenting the image that has had the redundant information removed by adding an average value of the image that has the redundant information removed to a standard derivation thereof.

7. An apparatus for a CT scan of a body part, wherein a marker is adapted to be positioned on the body part, the apparatus comprising:
    a scout scan component for performing a scout scan of an area that contains the body part with the marker positioned thereon to acquire a scout image;
    a position acquisition component for detecting the marker in the scout image to acquire position information of the marker; and
    a navigation component for using said position information of the marker to navigate the CT scan during the CT scan of the body part.

8. The apparatus according to claim 7, wherein the marker is a wire-like marker positioned on the body part to be parallel to a Z-axis in a CT scan system.

9. The apparatus according to claim 8, wherein the navigation component is configured to:
use the position information of the marker to set a Z-axis scan range in the CT scan, and/or use the position information of the marker to set a Y-axis scan range in the CT scan,
wherein at least one of the Z-axis scan range and the Y-axis scan range is used to perform the CT scan.

10. The apparatus according to claim 9, wherein, in a D4D-CT scan, the position information of the marker is used to set the Y-axis scan range in the CT scan.

11. The apparatus according to claim 9, wherein the Z-axis scan range in the CT scan is set based on positions of two endpoints of said wire-like marker and a start position of the scout scan.

12. The apparatus according to claim 7, wherein the position acquisition component is configured to apply a linear difference operator to the scout image at least once to acquire an enhanced image, wherein the linear difference operator is acquired based on a shape and an orientation of the marker.

13. The apparatus according to claim 12, wherein the position acquisition component is configured to perform pre-processing on the enhanced image, wherein the pre-processing comprises:
removing redundant information from the enhanced image; and
segmenting the image that has had the redundant information removed.

14. The apparatus according to claim 13, wherein removing the redundant information from the enhanced image comprises at least one of:
identifying pixel points with pixel values that are below a preset threshold as background; and
segmenting the image that has had the redundant information removed by adding an average value of the image that has the redundant information removed to a standard derivation thereof.

15. The apparatus according to claim 13, wherein the segmented image is processed in the following steps:
based on the shape and the orientation of the marker, removing noise of a candidate graphic of the marker in the image, and filling gaps of the candidate graphic; and
slenderizing the candidate graphic.

16. The apparatus according to claim 15, wherein a pattern recognition is at least based on one of: a physical length of the marker, a shape of the candidate graphic in the image, and whether there are other graphics on an extension line of the candidate graphic.

17. The apparatus according to claim 13, wherein the position acquisition component is configured to perform pattern recognition on the pre-processed image to acquire the position information of the marker in the scout image.

18. The apparatus according to claim 17, wherein the position acquisition component is further configured to convert image position information of the marker in image space to physical position information of the marker in the CT scan system.

19. A method for a medical scan of a body part, wherein a marker is adapted to be positioned on the body part, the method comprising:
performing a scout scan of an area that contains the body part with the marker positioned thereon to acquire scout data;
reconstructing a scout image from the scout data, the scout image including the marker;
detecting the marker in the scout image to acquire position information of the marker; and
using the position information of the marker to navigate the medical scan.

20. The method according to claim 19, wherein the medical scan comprises a CT scan and an MRI scan.

21. The method according to claim 19, wherein using the position information of the marker to navigate the medical scan comprises setting a scan range for at least one of a Z-axis and a Y-axis based on the position information of the marker, and performing the medical scan with the scan range.

* * * * *